(12) United States Patent
Robbins, III

(10) Patent No.: US 6,922,646 B2
(45) Date of Patent: Jul. 26, 2005

(54) METHOD AND SYSTEM FOR RANDOM SAMPLING

(75) Inventor: Sanford H. Robbins, III, Annapolis, MD (US)

(73) Assignee: Randomperfect, LLC, Annapolis, MD (US)

(*) Notice: Subject to any disclaimer, the term of this patent is extended or adjusted under 35 U.S.C. 154(b) by 193 days.

(21) Appl. No.: 10/261,216

(22) Filed: Sep. 30, 2002

(65) Prior Publication Data

US 2004/0064278 A1 Apr. 1, 2004

(51) Int. Cl.$^7$ ............................................... G06F 19/00
(52) U.S. Cl. .................... 702/84; 702/83; 702/122; 702/22; 702/182; 702/183
(58) Field of Search .......................... 422/63, 64, 65, 422/68.1; 435/287.1, 287.2, 287.3; 436/132, 43, 48, 50; 700/48; 702/122, 182, 183, 22, 83, 84; 705/4

(56) References Cited

U.S. PATENT DOCUMENTS

| | | | |
|---|---|---|---|
| 4,472,784 A | 9/1984 | Blachman | 702/83 |
| 4,580,226 A | 4/1986 | Bennison | 700/219 |
| 5,461,570 A | 10/1995 | Wang et al. | 700/110 |
| 5,532,941 A | 7/1996 | Lin | 702/84 |
| 5,696,686 A | 12/1997 | Sanka et al. | 700/110 |
| 5,937,364 A | 8/1999 | Westgard et al. | 702/83 |
| 6,027,691 A * | 2/2000 | Watts et al. | 422/64 |
| 6,269,276 B1 | 7/2001 | Akhavan et al. | 700/97 |
| 6,556,951 B1 * | 4/2003 | Deleo et al. | 702/183 |

FOREIGN PATENT DOCUMENTS

JP 63251309 4/1990

* cited by examiner

Primary Examiner—John Barlow
Assistant Examiner—Stephen Cherry
(74) Attorney, Agent, or Firm—Lieberman & Brandsdorfer, LLC

(57) ABSTRACT

A method and system for providing quality control through random sampling is provided. The system includes several modules for supporting the random sampling. A first module is adapted to select a technician for performing a procedure in association with an instrument. A second module is adapted to identify a random position for placement of a quality control on the equipment. A third module is adapted to select a random time interval for the selected technician to perform the procedure. A fourth module is adapted to select any analyzable specimen for repeat analysis or for selecting a patient sample for repeat analysis. Accordingly, the four modules enable random selection of several variables including the selection of the technician, instrument, position, time, and repeat testing.

19 Claims, 5 Drawing Sheets

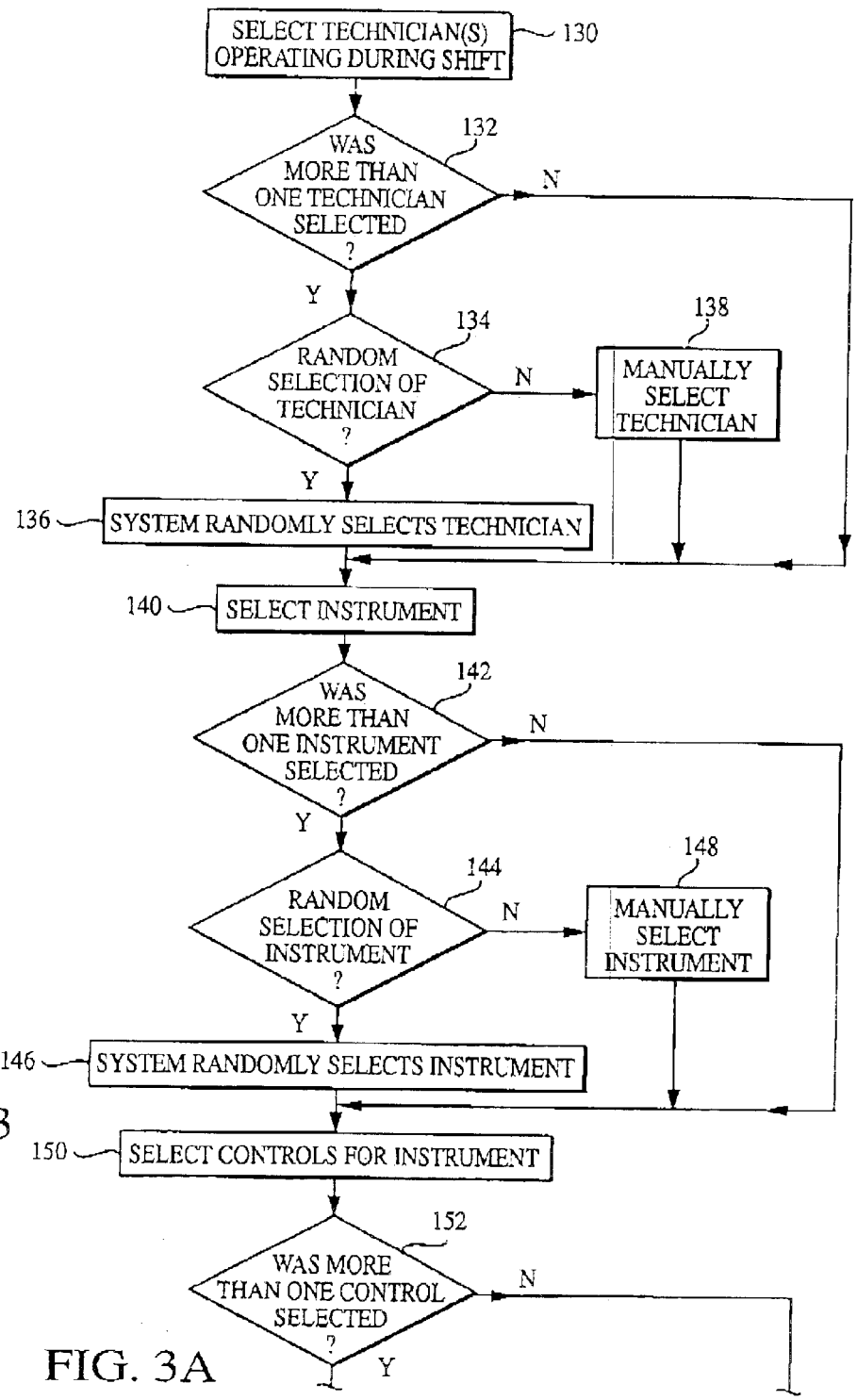

METHOD AND SYSTEM FOR RANDOM SAMPLING

BACKGROUND OF THE INVENTION

1. Technical Field

This invention relates to quality control and quality assurance in a laboratory. More specifically, the invention relates to assuring and controlling quality of equipment and personnel in a laboratory.

2. Description of the Prior Art

Quality control in the clinical laboratory is an accepted component of maintaining a standard of operation for laboratory equipment. It is mandated by the federal government and all major laboratory accrediting organizations. Quality controls are samples of assayed materials of known values as established by repetitive analysis. In the clinical laboratory, these samples are processed at periodic intervals in a manner that approximates patient testing. Quality control samples must be run at more than one concentration level. The stated values of controls are used as target values. Control results are analyzed using statistical parameters to determine if an instrument and/or reagent system is in control for a given run of patient test results. A variety of complex statistical methods exist for determination of acceptability of quality control results prior to releasing patient test results. Control results are recorded and plotted on charts and evaluated by technical staff to detect problems and trends in sample testing.

Modern quality control theory is predicated on the assumption that quality controls are to be performed at a frequency within which the accuracy and precision of the measuring system is expected to be stable based upon manufacturer's recommendations. However, both random and systematic errors are known to occur at some level of frequency within any given testing system. The goal of quality control is to detect these errors before false patient test results are released. Standard practices of quality control in today's clinical laboratory appears to be biased. The biases occur because the interval at which controls are run are generally pre-determined and defined by a given laboratory in a manner which is arbitrary or based upon convenience. To eliminate these biases, controls should be run in a completely random manner. It is prescribed that control samples should be tested in the same manner as patient specimens. Current biases in quality control methods with regard to time interval and position placement prevent simulation of actual patient testing conditions by controls.

In a hospital laboratory, it is common practice to run quality controls at the beginning of each shift. Some laboratories run quality controls at a defined interval between patient samples. Environmental conditions such as temperature, humidity, electrical source variation, and other factors may vary during the time period in which patient samples are tested. Failure to move quality controls around over time may result in failure of quality controls to detect testing problems. Most modern laboratory instruments are configured in a manner that accommodates running multiple patient samples at a given time. Common instrument configurations adapted to receive multiple test samples include testing wheels, racks, and plates with multiple wells. Since patient samples may be run in any of the positions on an instrument, it is logical that quality control samples should have an equal chance of being placed in any position to more accurately simulate actual patient testing conditions. In fact, some instrument manufacturers have included internal wells or vessels for storage of control materials that are separate from the portion of the instrument within which patient samples are placed for testing. Although this may be convenient to the technologist, it clearly does not simulate actual patient testing conditions. The chemical reaction may be identical, but the mechanical steps that precede the reactions clearly are not. Random placement of control materials in any of the positions on an instrument for which patient samples have a chance of being placed more closely simulates actual patient testing conditions. Accordingly, there is a need for a method for randomly selecting a position in which to place a control sample on a given instrument.

Ideally, randomization of as many variables as possible should provide the closest simulation of quality control testing to actual patient testing conditions. For a variety of reasons, it may not be practical or possible to randomize all variables at one time and still perform controls in a way that will allow review prior to releasing patient test results. However, by randomly selecting among several factors that contribute to proper operation of the laboratory equipment, a laboratory will be able to perform quality control in a manner that closely simulates actual patient testing conditions.

In addition to physical placement of a quality control on a laboratory instrument to insure proper function of the equipment, there is also a factor of human error that must be acknowledged. Cross training of technologists is common practice in today's clinical laboratory. Multiple operators may be performing testing on one instrument at any given time. It is necessary for operators to maintain competency and adequate skill levels on all equipment that they may be using for patient testing. Randomization of operator scheduling assures ongoing experience in all areas for which the operator may be required to work. One method of competency testing is to randomly repeat tests for patient samples by a second skilled individual. One method of maintaining quality assurance is to repeat the work by a second skilled individual and to compare the results for agreement. Accordingly, there is a need to periodically assess the skills and competency of operators in an unbiased manner.

SUMMARY OF THE INVENTION

This invention comprises a system for maintaining quality control and quality assurance in a clinical laboratory.

In a first aspect of the invention, a method of conducting quality control is provided. The method includes selecting personnel assigned to an instrument to perform a procedure, identifying a random position for placement of a quality control on the instrument, and selecting a random time interval for the personnel to perform the procedure. The step of selecting the personnel may include a random selection process from a list of personnel authorized to operate the instrument. The step of identifying the position for placement of the quality control may include randomly assigning the position. The position assignment may be indicated to the operator through a visual display. The step of selecting a random time interval may include randomly selecting the time from a defined time interval. The method may also include the step of randomly generating an assignment for authorized personnel. The assignment preferably includes an operator assigned to the equipment, placement of the quality control on a specific instrument, the time selection to test the control, and random selection of instrument work assignments in a specified time interval.

In a second aspect of the invention, a method of conducting quality assurance is provided. The method includes selecting a sample for repeating, selecting an individual for repeating a test of the select sample, and randomly selecting any analyzable sample for repeating. The analyzable sample is selected from a defined group of samples performed by a specific individual. The step of selecting an individual for repeating a test of the selected sample may include randomly selecting the individual. The step of selecting the sample may include selecting the sample from a defined group of samples according to a patient. The sample selected may include blood, body fluid, a cytology slide, a surgical pathology slide, a hematology slide, a body fluid slide, and any other analyzable sample, and combinations of the listed samples. In addition, the method may also include the step of comparing an original set of procedure results and a repeat set of procedure results.

In a third aspect of the invention, an article comprising a computer-readable signal bearing medium is provided. The article includes means in the medium for randomly selecting placement of a sample for testing, means in the medium for randomly selecting personnel to perform the testing of the selected sample, and means in the medium for randomly selecting a time interval for the selected personnel to perform testing of the selected sample. The medium is preferably selected from the group consisting of a recordable data storage medium and a modulated carrier signal. The means for randomly selecting placement of the sample preferably includes randomly selecting an operator to test laboratory equipment controls. The means for randomly selecting personnel to perform testing preferably includes randomly selecting the personnel from a list of personnel authorized to operate a selected instrument. The means for randomly selecting a time interval preferably includes randomly defining the time from a defined time interval.

In a fourth aspect of the invention, a system to maintain quality control in a laboratory is provided. The system includes a module adapted to select a technician assigned to operate laboratory equipment to perform a procedure, a module adapted to identify a random position for placement of a quality control on the selected equipment, and a module adapted to select a random time interval for the selected technician to conduct the procedure. The selection module is preferably adapted to randomly select the technician from a list of authorized technicians for the selected equipment. The placement identification module is preferably adapted to randomly assign a position for placement of the quality control. The random time selection module is preferably adapted to randomly select the time from a defined time interval. The system may also include a module adapted to randomly generate an assignment for the selected technician. The assignment may include an operator assigned to the equipment, placement of the quality control on a specific instrument, the time selection for testing of the quality control, and random selection of instrument work assignments in a specified time interval. The random position module may also include a visual display adapted to indicate a location to the selected technician for placement of the quality control.

In a fifth aspect of the invention, a system to maintain quality assurance in a laboratory is provided. The system includes a module adapted to select a sample to be repeated, a module adapted to select an individual to repeat a test of the selected sample, and a module adapted to randomly select any analyzable sample to be repeated. The analyzable sample is selected from a defined group of samples performed by a specific individual. The individual selection module may be adapted to randomly select the individual. The sample selection repeat module may be adapted to select the sample from a defined group of samples according to a patient. The sample may consist of blood, body fluids, a cytology slide, a surgical pathology slide, a hematology slide, a body fluid slide, or any other analyzable sample. The system may also include a module adapted to compare an original set of procedure results and a repeat set of procedure results.

Other features and advantages of this invention will become apparent from the following detailed description of the presently preferred embodiment of the invention, taken in conjunction with the accompanying drawings.

DESCRIPTION OF THE PREFERRED EMBODIMENT

Overview

In a clinical laboratory quality control and quality assurance activities are part of standard practice. The modules herein provide unique methods for quality control performance using a method of randomization to more closely simulate actual patient testing conditions and eliminate selection biases. Other modules provide methods of quality assurance that include random selection of blood, body fluid, cytology, surgical pathology, and other tests for repeat analysis. An interactive database is provided for data analysis, reporting, and storage.

Technical Background

In managing quality control and quality assurance of both personnel and equipment in a clinical laboratory, it is important to monitor the accuracy of the product as well as the professional capabilities of the personnel operating the testing equipment. The preferred embodiment provides a product that enables random selection of a plurality of parameters in the laboratory environment in order to maintain the quality of the testing. The product is computer implemented and includes several modules that may act independently or together depending upon selection of the individual operating the product.

Figure 1:
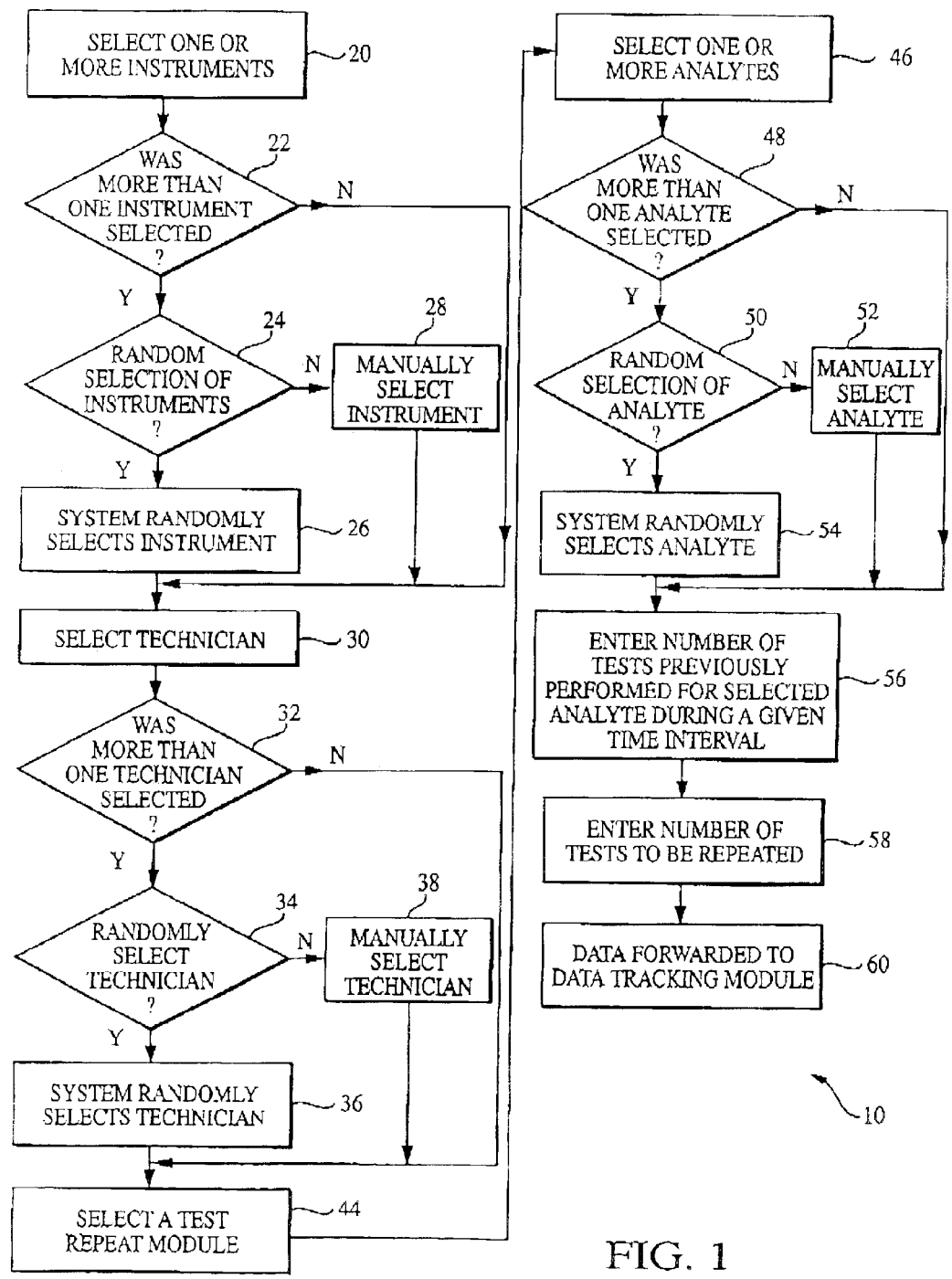
FIG. 1 is a flow chart illustrating a method for randomly selecting tests for repeat analysis according to the preferred embodiment of this invention, and is suggested for printing on the first page of the issued patent.

The first module is used to provide quality assurance of laboratory personnel. This module enables an operator of the product to randomly select tests for repeat analysis thereby testing the competency of the equipment operator. FIG. 1 is a flow chart 10 illustrating the steps in providing quality assurance by repeating select tests. The first step 20 in this module is to select the instrument in the laboratory on which the test is to be conducted. The operator of the module may select one instrument or several instruments in the laboratory. If the operator selects more than one instrument 22, they will be queried to determine if they want a random selection process to select the instrument on which the test is to be conducted 24. By providing a positive response to the query at step 24, the computer will randomly select one of the instruments for the repeat study through a random selection algorithm 26. However, if at step 24 the operator provides a negative response, they may manually select an instrument 28.

Following selection of an instrument, the operator must select a technician to repeat the analysis 30. The operator of the program may select one technician from an available list of technicians qualified to operate the selected instrument(s), or the operator may select several technicians from the available list. If the operator selects more than one technician 32, they will be queried to determine if they want a random selection process to select the technician to conduct the test 34. By providing a positive response to the query at step 34, the computer will randomly select one technician to perform the repeat analysis through a random selection algorithm 36. However, if at step 34 the operator provides a negative response, they may manually select a technician 38.

Following the selection of the technician at steps 36 or 38, the operator of the computer selects a test repeat module on the selected instrument 44. The selection of a test may include a variety of tests performed in the laboratory, including blood, body fluids, and any other analyzable sample. Following the selection of the test module at step 44, the operator selects an analyte 46. Similar to step 32, the computer module will conduct a query 48 to determine if more than one analyte was selected at step 46. If more than one analyte was selected, the operator will be queried to determine if they want a random selection process to select the analyte for testing 50. By providing a positive response to the query at step 50, the computer will randomly select one analyte for the repeat analysis through a random selection algorithm 54. Alternatively, the operator may manually select the analyte 52. Following the selection of the analyte at steps 52 or 54, the operator must enter the number of tests that have been previously performed for the selected analyte during a given time period 56. In addition, the operator must select the number of tests to be repeated 58. The random selection algorithm then selects one or more combinations of a test, an operators, and a instrument to be repeated. Thereafter, the test, equipment, and operator combination are sent to a data tracking module 60. Accordingly, the module illustrated in FIG. 1 provides a method for selecting repetition of tests on equipment to be performed by an operator, wherein the selection of variables may be specific or may be randomly selected through a random selection algorithm.

Figure 2:
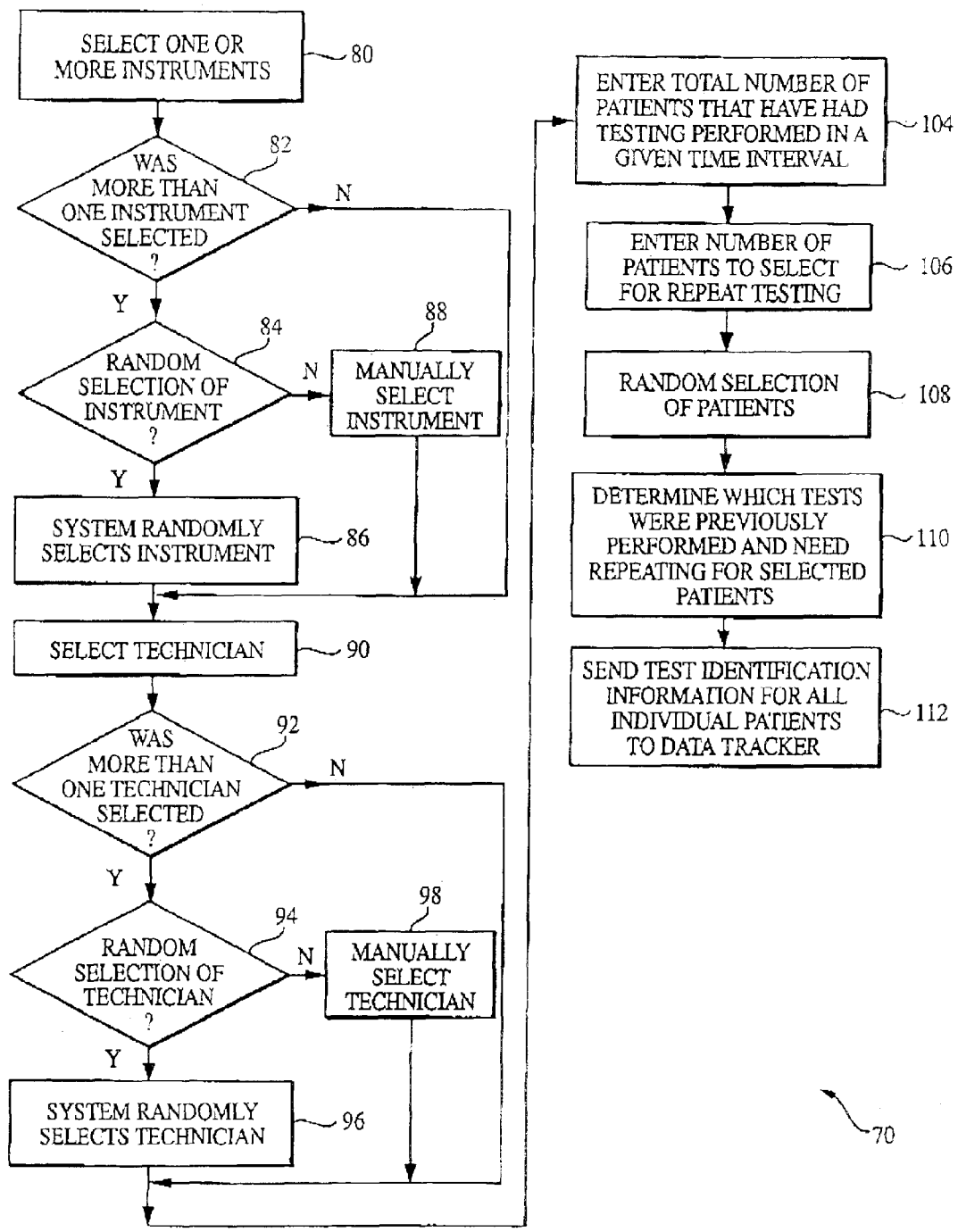
FIG. 2 is a flow chart illustrating a method for repeating selected tests.

The module outlined in FIG. 1 is a method for repeating specific tests to assure the results of the test conducted. This module may be modified to repeat specific tests according to patient information. FIG. 2 is a flow chart 70 illustrating the steps in providing quality assurance by repeating select tests. The first step 80 in this module is to select the instrument in the laboratory on which the test is to be conducted. The operator of the module may select one instrument or several instruments in the laboratory. If the operator selects more than one instrument 82, they will be queried to determine if they want a random selection process to select the instrument on which the test is to be conducted 84. By providing a positive response to the query at step 84, the computer will randomly select one of the instrument for the repeat study through a random selection algorithm 86. However, if at step 84 the operator provides a negative response, they may manually select an instrument 88. Following selection of an instrument, the operator must select a technician to repeat the analysis 90. The operator of the program may select one technician from an available list of technicians qualified to operate the selected instrument(s), or the operator may select several technicians from the available list. If the operator selects more than one technician 92, they will be queried to determine if they want a random selection process to select the technician 94. By providing a positive response to the query at step 94, the computer will randomly select one technician from the list of technicians selected by the operator to perform the repeat analysis 96. The random selection process is generated through a random selection algorithm. However, if at step 94 the operator provides a negative response, they may manually select a technician 98.

Following the selection of the technician, the operator of the computer module enters the total number of patients that have had testing performed in a given the interval 104. Thereafter, the operator must enter the number of patients for which they want tests repeated 106. A random selection algorithm then randomly selects patients for repeat testing 108 from a list of patients provided at step 106. The operator must determine which tests were previously performed and need repeating for each selected patient 110. The test identification information is sent to a module adapted to track data information pertaining to the tests conducted 112. Accordingly, this random selection module enables an operator to invoke a random selection algorithm for the instrument, technician and patient.

Figure 3B:
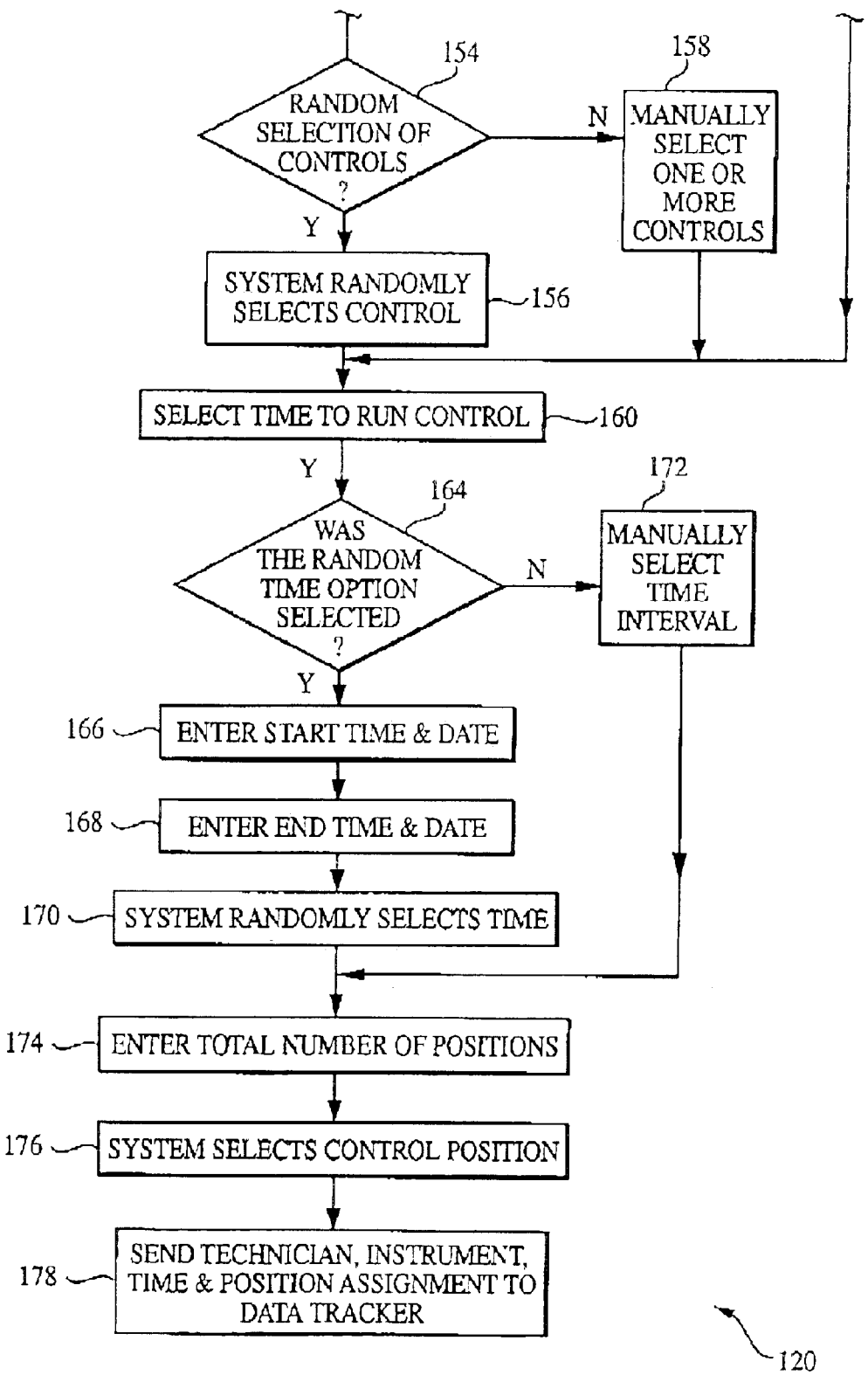
FIG. 3 is a flow chart illustrating a method for randomly scheduling testing operations.

A third module in the product is a positioner to maintain quality control of the equipment and test results. The positioner is a module that can be used to schedule quality control operations. The operator of the module may select among the parameters of time, technician and/or position on a specific instrument in the laboratory. FIG. 3 is a flow chart 120 illustrating the process of operating the positioner module. The operator of the module selects a technician operating instruments during a specific work shift 130. If the operator selects more than one technician 132, they will be queried to determine if they want a random selection algorithm to process and select a technician 134. By providing a positive response to the query at step 134, the computer will randomly select one of the technicians from the list of selected technicians for the study through a random selection algorithm 136. If the operator does not want a technician to be randomly selected, they must manually select a specific technician for operation of the instruments at step 138. The operator of the module then proceeds with selection of an instrument in the laboratory upon which the control is to be conducted 140. If the operator selects more than one instrument 142, they will be queried to determine if they want a random selection algorithm to select the instrument 144. By providing a positive response to the query at step 144, a random selection algorithm will be invoked to randomly select one of the instruments in the laboratory upon which the quality control should be placed from the list of instruments selected in step 146. If the operator does not want an instrument to be randomly selected, they must select a specific instrument at step 148. Once the operator and instrument selections have been made, the operator of the module must select a quality control for the instrument 150. The operator may select a specific quality control, or again, may allow the module to randomly select a control from a list of quality controls available for the instrument. If the operator wants a specific quality control they must limit their selection at step 150 to one specific quality control. Otherwise, if at step 152 it is determined that more than one quality control is selected, the operator will be queried to determine if they want to invoke a random selection algorithm 154. A positive response to the query at 154 will result in the activation of a random selection algorithm 156 to randomly select the quality control from the list provided at step 150. Alternatively, if the operator does not choose to invoke the random selection algorithm, they may manually select one or more quality controls from the list provided 158. Following the selection of the quality controls, the operator must select the time for the selected technician to run the selected control 160. The operator has a choice of two time variables: an operator selected time or a randomly selected time. The randomization of the quality control process enables the operator to simulate actual patient conditions.

Following the selection of the operator, instrument and time for running of the controls, the operator of the module must indicate a time interval in which the controls are to be run on the selected instrument by the selected technician. If the operator selects more than one time interval at step 162, they will be queried to determine if they want a random selection algorithm to select the time interval 164. By providing a positive response to the query at step 164, the operator will be prompted to enter a start date and a start time 166. Thereafter, the operator will be prompted to enter an end date and time 168. The module will then invoke a random selection algorithm to randomly select the time to run the quality control 170. If the operator does not want the time to be randomly selected at step 164, they must manually select a specific time interval at step 172. Following the selection of the time interval, the operator must enter the total number of positions available for placement of the quality control(s) 174 and patient samples. The module will then provide a visual depiction of the number of patient samples as well as controls to be run in the test batch. The operator is provided an opportunity to deselect any positions on the instrument that are not eligible for placement of the control. A display apparatus associated with the module will provide a visual depiction of where to place each control on the selected instrument. The module will then invoke a random selection algorithm to select position placement for the control(s) 176. The operator will be given a choice to send the data to the data tracking module, and offered an opportunity to print the quality control assignment information. Accordingly, the positioner module provides the opportunity to individually or randomly determine proper operation of instruments by the technicians assigned to operate the instruments.

Figure 4:
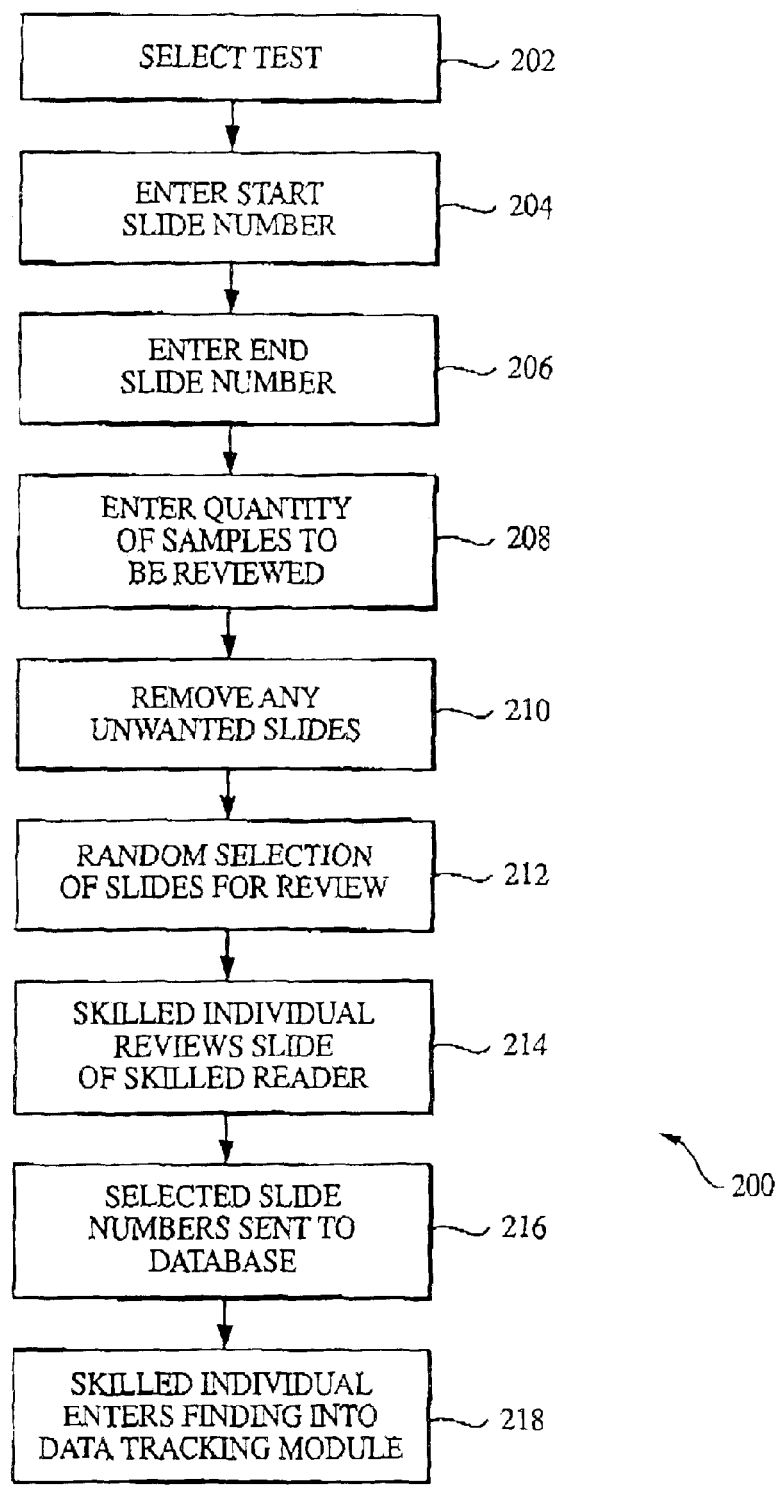
FIG. 4 is a flow chart illustrating a method for randomly selecting slides for repeat analysis for quality assurance purposes.

A fourth module is provided to maintain quality assurance of the competency of the personnel reviewing the slides. FIG. 4 is a flow chart 200 illustrating the process involved in maintaining quality assurance of a Pathologist or other skilled individual in reviewing laboratory slides. The first step is for the operator of the module to select a test for which the quality assurance will be conducted 202. Each slide in a test is assigned a number. The operator must enter a number from among the slides where they want to initiate the quality assurance 204. Thereafter, the operator must enter a number from among the slide indicating where the operator wants to conclude the quality assurance 206. After the range of slides has been entered into the module 204, 206, the operator must enter the number of slide samples they want reviewed 208. The operator is then provided the opportunity to remove any unwanted slides 210. Unwanted slides may includes slides that have already received an abnormal reading, are unavailable, or any other slides the operator choose to deselect for various purposes. The modules then randomly selects the slides to be reviewed 212 from the range of slides provided in steps 204 and 206, and the quantity of slides selected for review at step 208. Random selection of the slides is processed through a random selection algorithm. The Reviewing Pathologist or other skilled individual reviews the slide of the original reader of the slides 214. The slide numbers selected for review are then sent to the data tracking modules 216. The Reviewing Pathologist or other skilled individual enters their findings from their review of the slides into the data tracking module 218. Accordingly, the quality assurance module provides a method and system for enabling a second skilled individual to review a random selection of sample slides previously reviewed by a first skilled individual.

In addition to the positioner module and the repeat modules, the apparatus includes a storage module for temporarily storing data results from the quality control modules. The storage module is an interface adapted to track data generated through each of the modules outlined in FIGS. 1, 2, 3 and 4. The data in the storage module may be processed to generate charts, graphs and a variety of statistical information. For example, the storage module may be used to determine if a particular repeated test has passed or failed the based upon the standard deviation of the statistical quality control data for that test. The quality control sample is generally accompanied by a mean value and a standard deviation value. A quality control sample can be compared to the expected quality control results to determine if the test results are within the acceptable limits. If the quality control sample result exceeds the mean by greater than 2.0 times the standard deviation in either direction, the operator will be provided with a warning message. However, if the quality control sample results exceeds the mean by greater than 3.0 times the standard deviation in either direction, the operator will be provided with a fail message. Accordingly, depending upon the module in use and the selected variables, the operator will be able to determine if: the quality control is within a compatible limit to release the test data, or the quality check performed by repeating selected tests indicates the system is functioning as expected or requires troubleshooting.

Advantages Over The Prior Art

The modules described herein in detail provide a means for monitoring laboratory equipment as well as assigned personnel in an unbiased manner. An operator of the modules may select among a variety of factors to invoke a random selection tool. This enables the variable factors to be processed through a random selection algorithm. In view of the recent federal legislation for requiring quality control samples to be tested in the same manner as patient specimens, a random selection module is essential for providing a true reproduction of actual testing of patient specimens. The random selection tools within the modules eliminate biases that may be present during the actual selection process.

Alternative Embodiments

It will be appreciated that, although specific embodiments of the invention have been described herein for purposes of illustration, various modifications may be made without departing from the spirit and scope of the invention. In particular, the invention is not limited to use in a clinical laboratory environment. Rather the modules may be applied in a variety of environments in which random selection is preferred or in which replication of natural selection processes are desired. The random selection algorithm may be computer implemented. Furthermore, the modules may be modified to automatically invoke the random selection algorithm upon selection by the operator of more than one variable parameter. This streamlining of the random selection process of the variable parameter(s) may also include automatically removing the technician who performed the original test from the list of technicians available for manual or random selection of a technician. In providing the quality assurance testing of the equipment and assigned technicians, it is desirable but not mandatory that the technician performing the repeat analysis be a different technician than the technician who performed the original test. The computer may perform a query to determine that the selected technician is different from the original technician. If the selected technician is the same as the original technician, then the technician selection will be discarded and the operator will be prompted to select another technician. Finally, the random selection algorithm may be modified to invoke different theories of random selection within the modules disclosed. Another use of the random repeat module could be for comparison of samples between two instruments. Accordingly, the scope of protection of this invention is limited only by the following claims and their equivalents.

I claim:

1. A computer implemented method of conducting quality control comprising:
   a. selecting personnel assigned to a corresponding instrument for performing a procedure;
   b. identifying a random position for placement of a quality control for said instrument; and
   c. selecting a random time interval for said selected personnel to perform said procedure.

2. The method of claim 1, wherein the step of selecting personnel includes randomly selecting said personnel from a list of personnel authorized to operate said instrument.

3. The method of claim 1, wherein the step of identifying a random position for placement of a quality control for said instrument includes randomly assigning said position.

4. The method of claim 1, wherein the step of selecting a random time interval for said selected personnel to perform said procedure includes randomly defining said time from a defined time interval.

5. The method of claim 1, further comprising randomly generating an assignment for authorized personnel.

6. The method of claim 5, wherein said assignment is selected from the group consisting of: an operator assigned to equipment, placement of said quality control on a specified instrument, time selection for testing of said quality control, random selection of an instrument work assignment in a specified time interval, and combinations thereof.

7. The method of claim 1, wherein the step of identifying a random position for placement of a quality control for said instrument includes visually indicating a location for placement of said quality control on said instrument to said operator.

8. An article comprising a computer-readable storage medium storing instructions comprising:
   instructions for randomly selecting placement of sample for testing;
   instructions for randomly selecting personnel to perform testing of the selected sample; and
   instructions for randomly selecting a time interval for said selected personnel to perform testing of the selected sample.

9. The article of claim 8, wherein the medium is selected from the group of: a recordable data storage medium and a modulated carrier signal.

10. The article of claim 8, wherein said instructions for randomly selecting placement of sample testing includes instructions for randomly selecting an operator to test laboratory equipment controls.

11. The article of claim 8, wherein said instructions for randomly selecting personnel to perform said sample testing includes instructions for randomly selecting said personnel from a list of personnel authorized to operate said instrument.

12. The article of claim 8, wherein said instructions for randomly selecting a time interval for said selected personnel to perform said sample testing includes instructions for randomly defining said time from a defined time interval.

13. A system to maintain quality control in a laboratory comprising:
   a module adapted to select a technician assigned to operate laboratory equipment to perform a procedure;
   a module adapted to identify a random position for placement of a quality control on the selected equipment; and
   a module adapted to select a random time interval for the selected technician to conduct the procedure.

14. The system of claim 13, wherein the selection module is adapted to randomly select the technician from a list of technicians authorized to operate said selected equipment.

15. The system of claim 13, wherein the placement identification module is adapted to randomly assign a position for placement of the quality control.

16. The system of claim 13, wherein the random time selection module is adapted to randomly select the time from a defined time interval.

17. The system of claim 13, further comprising a module adapted to randomly generate an assignment for said selected technician.

18. The system of claim 17, wherein said assignment is selected from the group consisting of: an operator assigned to equipment, placement of said quality control on a specified instrument, time selection for testing of said quality control, random selection of instrument work assignments in a specified time interval, and combinations thereof.

19. The system of claim 13, wherein said random position module includes a visual display adapted to indicate a location for placement of said quality control to said selected technician.

* * * * *